United States Patent [19]
Miyazaki et al.

[11] Patent Number: 5,367,105
[45] Date of Patent: Nov. 22, 1994

[54] PROCESS AND DEVICE FOR PRODUCTION OF ALLYL CHLORIDE

[75] Inventors: Hidetaka Miyazaki, Tokuyama; Toshiaki Hasegawa, Kawaguchi; Yoshihiko Kajimoto, Tokuyama; Susumu Mochida, Yokohama, all of Japan

[73] Assignees: Tokuyama Corporation, Yamaguchi; Nippon Furnace Kogyo Kaisha, Ltd., Kanagawa, both of Japan

[21] Appl. No.: 139,851

[22] Filed: Oct. 22, 1993

[30] Foreign Application Priority Data

Oct. 23, 1992 [JP] Japan ................... 4-286041

[51] Int. Cl.$^5$ ............................................. C07C 17/10
[52] U.S. Cl. .................................................. 570/234
[58] Field of Search ........................................ 570/234

[56] References Cited
FOREIGN PATENT DOCUMENTS

| | | |
|---|---|---|
| 0107215 | 5/1984 | European Pat. Off. . |
| 0297238 | 1/1989 | European Pat. Off. . |
| 47013006 | 4/1972 | Japan . |
| 61040232 | 8/1984 | Japan . |

*Primary Examiner*—Howard T. Mars
*Attorney, Agent, or Firm*—Birch, Stewart, Kolasch & Birch

[57] ABSTRACT

A process for the production of allyl chloride, which comprises introducing propylene and chlorine into a reactor having at least one propylene-injection opening and at least one chlorine-injection opening, these openings being independent of each other, through the respective injection openings, and reacting them in a vapor phase, wherein propylene and chlorine are introduced into the reactor by injecting them in almost the same direction from the propylene-injection opening and the chlorine-injection opening which is closest to said propylene-injection opening, with a linear velocity in the propylene-injection opening, calculated as a value of at 300° C. and 1 kg/cm$^2$.G, of 100 m/sec or higher and a linear velocity of the chlorine-injection opening, calculated as a value of at 100° C. and 1 kg/cm$^2$.G, of 70 m/sec or higher, and the propylene-injection opening and the chlorine-injection opening are situated to meet the following expression (1), $$0.5 \leq L/(d_p+d_c) \leq 20 \qquad (1)$$

wherein dp is a diameter of the propylene-injection opening, dc is a diameter of the chlorine-injection opening which is closest to said propylene-injection opening, and L is a distance between centers of these two injection openings.

9 Claims, 2 Drawing Sheets

PROCESS AND DEVICE FOR PRODUCTION OF ALLYL CHLORIDE

BACKGROUND OF THE INVENTION

1. Field of the Invention

This invention relates to a process and a device for the production of allyl chloride by reacting propylene with chlorine in a vapor phase.

2. Prior Art

A process for the production of allyl chloride by reacting propylene with chlorine in a vapor phase has been well known. For example, Japanese Patent Publication Sho 47-13,006 (13,006/1972) discloses a process in which injection openings for propylene and chlorine are alternately situated circumferentially in an inside surface of a reactor whose horizontally sectional shape is almost circular, and propylene and chlorine are injected in a tangential direction of the circle for reaction.

This process can produce allyl chloride with relatively high selectivity without operational troubles such as clogging of a reactor owing to formation of carbon as a by-product, etc., and is, therefore, an excellent process. In this process, however, the formation of carbon cannot completely be suppressed, with a result that the obtained allyl chloride turns black due to carbon formed. Accordingly, clear allyl chloride cannot be provided without purification.

SUMMARY OF THE INVENTION

It is an object of this invention to provide a process for the production of allyl chloride with good selectivity by reacting propylene with chlorine, as well as a device that can be used in said process.

Another object of this invention is to provide a process for the production of allyl chloride which can substantially prevent coloration owing to formation of carbon as a by-product and obtain sufficiently clear allyl chloride without purification, as well as a device that can be used in said process.

In accordance with this invention, there is first provided a process for the production of allyl chloride, which comprises introducing propylene and chlorine into a reactor having at least one propylene-injection opening and at least one chlorine-injection opening, these injection openings being independent of each other, through the respective injection openings, and reacting them in a vapor phase, wherein propylene and chlorine are introduced into the reactor by injecting them in almost the same direction from the propylene-injection opening and the chlorine-injection opening which is closest to said propylene-injection opening, with a linear velocity in the propylene-injection opening, calculated as a value of at 300° C. and 1 kg/cm².G, of 100 m/sec or higher and a linear velocity in the chlorine-injection opening, calculated as a vale of at 100° C. and 1 kg/cm².G, of 70 m/sec or higher, and the propylene-injection opening and the chlorine-injection opening are situated to meet the following expression (1), $$0.5 \leq L/(dp+dc) \leq 20 \tag{1}$$

wherein dp is a diameter of the propylene-injection opening, dc is a diameter of the chlorine-injection opening which is closest to said propylene-injection opening, and L is a distance between centers of these two injection openings.

In accordance with this invention, there is secondly provided a device for the production of allyl chloride, said device having at least one injection opening of propylene and at least one chlorine-injection opening, these injection openings being independent from each other, wherein the propylene-injection opening and the chlorine-injection opening are situated to meet the following expression (1), $$0.5 \leq L/(dp+dc) \leq 20 \tag{1}$$

wherein dp is a diameter of the propylene-injection opening, dc is a diameter of the chlorine-injection opening which is closest to this propylene-injection opening, and L is a distance between centers of these two injection openings.

The aforesaid objects of this invention are achieved by the above inventions.

This invention will be described in more detail below, which makes clear further objects and advantages of this invention.

DETAILED DESCRIPTION OF THE INVENTION

Figure 1:
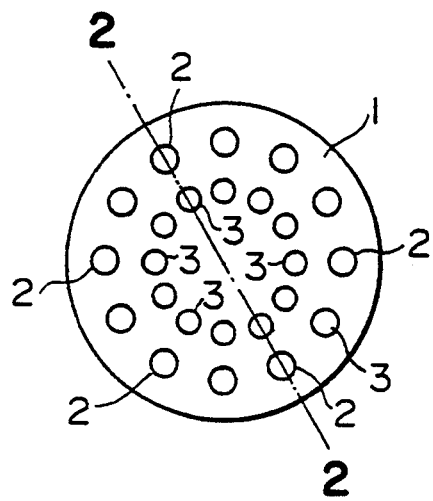
FIG. 1 is a schematic view of a nozzle as one embodiment used in this invention when an injection opening in a tip of the nozzle is seen from an axial direction of the nozzle.

In this invention, allyl chloride is produced by introducing propylene and chlorine from injection openings independent of each other into a reactor and reacting them in a vapor phase. In order to introduce propylene and chlorine into the reactor, a nozzle having injection openings at its tip is ordinarily used. A nozzle for propylene and a nozzle for chlorine may be separately provided. Or, when an propylene-injection opening and an chlorine-injection opening are formed independently from each other, one nozzle having both the injection openings may also be employed.

In a vapor phase reaction which is conducted by blowing two kinds of gases into a reactor, a double tube-type nozzle having concentric circlar partitions is at times used wherein the two gases are injected at the same time by passing through the inside and the outside thereof. In this invention, such double tube-type nozzle cannot be used because it does not meet the below-described relation of the diameters of the injection openings for propylene and chlorine and the distance between the centers of said injection openings.

In this invention, the injection openings are located to meet the following expression (1).

$$0.5 \leq L/(dp+dc) \leq 20 \tag{1}$$

wherein dp is a diameter of the propylene-injection opening, dc is a diameter of the chlorine-injection opening which is closest to this propylene-injection opening, and L is a distance between centers of these two injection openings.

By meeting the above relation, in combination with the conditions of the linear velocities in the injection openings for propylene and chlorine, formation of carbon is decreased, an amount of a by-product 1,2-dichloropropene is reduced, and selectivity for allyl chloride is improved.

In order to further improve selectivity for allyl chloride and notably suppress the amount of carbon formed as a by-product, it is preferable that the relation of the diameter of the propylene-injection opening, the diameter of the chlorine-injection opening which is closest to this propylene-injection opening and the distance between their centers satisfies the following expression (2).

$$1 \leq L/(dp+dc) \leq 10 \tag{2}$$

The diameter dp of the propylene-injection opening is preferably 0.5 to 150 mm, and the diameter dc of the chlorine-injection opening is preferably 0.3 to 100 mm. The distance L between the centers of the injection openings for propylene and chlorine is preferably 0.4 to 2,500 mm.

The number of the injection opening(s) for propylene is preferably 1 to 200, more preferably 2 to 100. The number of the injection opening(s) for chlorine is preferably 1 to 200, more preferably 2 to 100.

When the injection openings for propylene and chlorine are provided in plural number, it is advisable that the propylene-injection opening is situated such that the chlorine-injection opening is arranged closer thereto than the other propylene-injection opening and that the chlorine-injection opening is situated such that the propylene-injection opening is arranged closer thereto than the other chlorine-injection opening.

The number of the propylene-injection opening(s) may be the same as, or different from, the number of the chlorine-injection opening(s). Preferable is that the numbers of both the injection openings for propylene and chlorine are the same.

Figure 2:
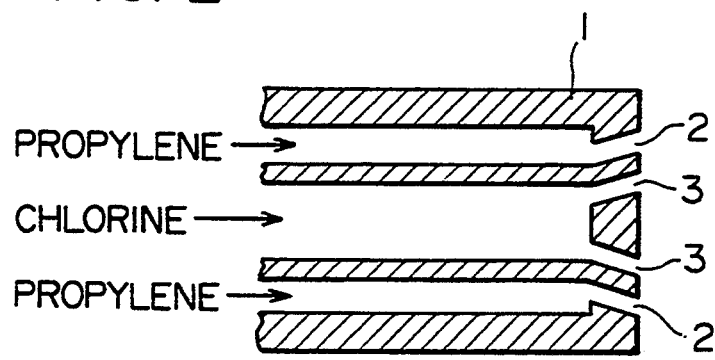
FIG. 2 is a schematic view of a section of the nozzle in FIG. 1 when cut at a plane A-A' parallel to the axial direction of the nozzle.

FIGS. 1 and 2 are each a schematic view of a nozzle having a plurality of injection openings 2 for propylene and a plurality of injection openings 3 for chlorine. FIG. 1 is a schematic view of the injection openings at the tip of the nozzle when seen from the axial direction of the nozzle. FIG. 2 is a schematic view of a section when cut at a plane A-A' parallel to the axial direction of the nozzle.

Figure 3:
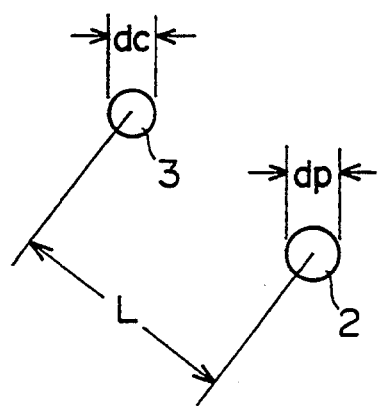
FIG. 3 is a schematic view showing a positional relation of the propylene-injection opening and the chlorine-injection opening.

At the tip of the nozzle, the injection openings 2 for propylene are concentrically arranged in the same flat surface outside the injection openings 3 for chlorine, and the injection openings 3 for chlorine are concentrically arranged in the same flat surface inside the injection openings 2 for propylene. As shown in FIG. 3, the relation of the diameter dp of any injection opening 2 for propylene, the diameter dc of the chlorine-injection opening 3 closest to said injection opening 2 for propylene and the distance L between the centers of these injection openings meets the aforesaid expression (1).

Figure 4:
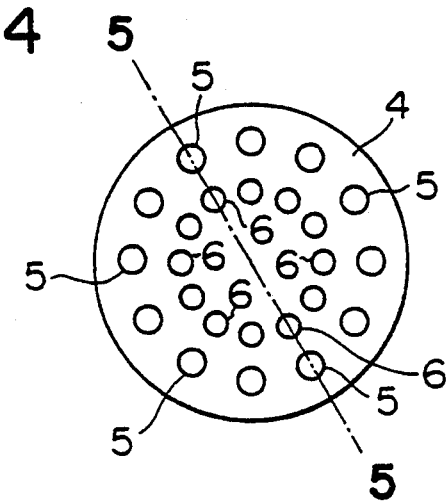
FIG. 4 is a schematic view of a nozzle as another embodiment used in this invention when an injection opening in a tip of the nozzle is seen from the axial direction of the nozzle.
Figure 5:
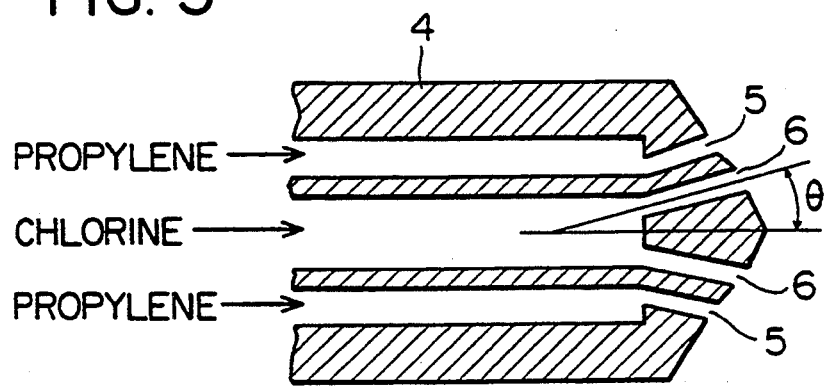
FIG. 5 is a schematic view showing a section of the nozzle in FIG. 4 when cut at a plane B-B' parallel to the axial direction of the nozzle.

FIGS. 4 and 5 are each a schematic view of another embodiment of the nozzle used in this invention. FIG. 4 is a schematic view of the injection openings at the tip of the nozzle 4 when seen from the axial direction of the nozzle 4. FIG. 5 is a schematic view of a section when cut at a plane B-B' parallel to the axial direction of the nozzle 4.

In a conical tip of the nozzle, the injection openings 5 for propylene are concentrically arranged in a conical side surface outside the injection openings 6 for chlorine, and the injection openings 6 for chlorine are concentrically arranged in the conical side surface inside the injection openings 5 for propylene. On this occasion, as is the case with the nozzle shown in said FIGS. 1 and 2, the relation of the diameters dp, dc and the distance L satisfies the aforesaid expression (1) too.

It is preferable that the injection openings for propylene and chlorine are arranged in almost the same flat surface as shown in FIG. 2. However, they may be arranged in the conical side surface and are not necessarily arranged in the same flat surface as shown in FIGS. 4 and 5. When propylene and chlorine are injected from their own independent nozzles, it sufficient that the nozzles are mounted such that the injection openings of the independent nozzles are located in almost the same flat surface.

The injection openings for propylene and chlorine preferably take a circular shape, but they may take the other shape such as an elliptical, square or rectangular shape. The diameter of the injection opening having the other shape is regarded as a diameter of a circle of the same area.

In this invention, propylene and chlorine are introduced into the reactor such that the linear velocity in the propylene-injection opening is 100 m/sec or higher and the linear velocity of the chlorine-injection opening is 70 m/sec or higher. By rendering the linear velocities of the injection openings of propylene and chlorine within the above ranges and meeting the aforesaid relation of the diameters of the injection openings of propylene and chlorine and the distance between the centers thereof, selectivity for intended allyl chloride can be improved enough and the amount of carbon formed be reduced. When the linear velocities in the injection openings of propylene and chlorine are set at 130 to 370 m/sec and 80 to 200 m/sec respectively, better results are given, and it is desirable.

The linear velocity in the propylene-injection opening is a value calculated as a value of at 300° C. and 1 kg/cm$^2$.G, and that in the chlorine-injection opening is a value calculated as a value of at 100° C. and 1 kg/cm$^2$.G.

The directions in which to inject propylene and chlorine from the respective injection openings that meet the relation of the above expression (1) are almost the same. That is, it is advisable that the lines showing the two injecting directions form a flat surface, and an angle formed by these lines is 0, i.e. that the directions are parallel. However, an angle which is within 30°, preferably within 10°, can sufficiently achieve the object of this invention.

When propylene and chlorine are injected from a nozzle with the injection openings of propylene and chlorine, angles formed by the injecting directions from the propylene-injection opening and the chlorine-injection opening closest to said propylene-injection opening and the axial direction of the nozzle are respectively preferably 0° to 60°. Especially when the angle is 5° to 10°, excellent results are obtained.

When using a nozzle having a plurality of the propylene-injection openings and a plurality of the chlorine-injection openings, it is advisable that viewed from a vertical direction relative to the axial direction of the nozzle, the chlorine-injection openings are arranged near the axis of the nozzle and the propylene-injection openings outside thereof. At this time, it is advisable that the injection openings for chlorine and propylene are circularly arranged so as to form a concentric circle.

The reaction conditions of propylene and chlorine can be employed from the known ranges. For example, the reaction temperature can be selected from 450° to 550° C., and the amounts of propylene and chlorine introduced are selected from a propylene/chlorine molar ratio of 3/1 to 5/1 respectively.

Figure 6:
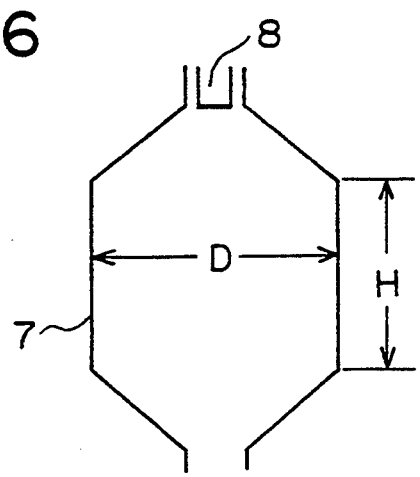
FIG. 6 is a schematic view of a vertical section of a device as one embodiment of this invention.

FIG. 6 is a schematic view of a vertical section of a device as an example used for the production of allyl chloride according to the process of this invention, said device comprising a reactor and a nozzle. A reactor 7 is so adapted that an intermediate portion of a cylinder is larger than diameters of upper and lower portions, and a nozzle 8 is inserted from the upper portion toward the lower portion of the cylinder. The direction of the nozzle 8 is almost vertical. From the nozzle 8, propylene and chlorine are injected into the reactor. Although part of the streams are circulated within the reactor, propylene and chlorine are reacted during passing of most of the streams through the reactor to thereby form allyl chloride, and the resulting allyl chloride is discharged from the lower portion of the reactor.

According to the process of this invention, allyl chloride can be produced with good selectivity. Besides, since formation of carbon is notably suppressed, the resulting allyl chloride does not turn black by carbon. Consequently, this invention can produce clear allyl chloride with good selectivity.

This invention is illustrated by the following Examples and Comparative Examples specifically.

EXAMPLES AND COMPARATIVE EXAMPLES

Allyl chloride was produced by reacting propylene with chlorine using a reactor of a shape shown in FIG. 6, which reactor is equipped with a nozzle provided with a plurality of the propylene-injection openings having the same diameter and a plurality of chlorine-injection openings having the same diameter, the numbers of injection openings for propylene and chlorine being the same, as shown in FIGS. 4 and 5. The reactor had an inner diameter (D) of 1,200 mm, a height (H) of 2,700 mm and an internal volume of 3,7 m³.

A variety of nozzles in which diameters of injection openings of propylene and chlorine and distances between the centers of these injection openings were shown in Table 1 were used. A chlorine gas of a normal temperature was fed to the injection openings formed circularly near the center of the nozzle, and a propylene gas preheated at about 350° C. was fed to the injection openings formed circularly outside thereof. Angles $\theta$ formed by the injecting directions of the injection openings for propylene and chlorine and the central axis are shown in Tables 1 and 2. The directions in which to inject propylene and chlorine from the propylene-injection opening and the chlorine-injection opening which is closest to said propylene-injection opening were made the same. The injection velocities of propylene and chlorine were set at values shown in Tables 1 and 2. Moreover, the feed rates of propylene and chlorine and the reaction temperature were set at values shown in Tables 1 and 2. Under such conditions, the reaction was carried out. Run No. 10 (Comparative Example) is a case of using a double tube-type nozzle.

An outlet gas, i.e. the reaction product, of the reactor was trapped with methylene chloride cooled with dry ice-methanol, and was analyzed by gas chromatography. The amount of carbon formed was shown in terms of a degree of coloration of an organic solvent used in the trapping. The results are shown in Tables 1 and 2.

In Table 1, the linear velocity of chlorine was a value calculated as a value of at 100° C. and 1 kg/cm², and the linear velocity of propylene was a value calculated as a value of at 300° C. and 1 kg/cm².

TABLE 1

| Run No. | Examples | | | | |
|---|---|---|---|---|---|
| | 1 | 2 | 3 | 4 | 5 |
| L [mm] | 60.9 | 31.4 | 48.5 | 72 | 142 |
| dc [mm] | 2.5 | 9.9 | 7.4 | 2.9 | 6.4 |
| dp [mm] | 6.2 | 21.5 | 16.5 | 6.1 | 13.9 |
| Number of propylene injection openings | 30 | 20 | 12 | 36 | 24 |
| Number of chlorine injection openings | 30 | 20 | 12 | 36 | 24 |
| L/(dp + dc) | 7 | 1 | 2 | 8 | 7 |
| Position of propylene injection openings | outside | outside | outside | outside | inside |
| Position of chlorine injection openings | inside | inside | inside | inside | outside |
| Injecting directions $\theta$ [°] | 5 | 5 | 5 | 5 | 5 |
| Linear velocity of chlorine gas [m/s] | 262 | 100 | 235 | 81 | 100 |
| Linear velocity of propylene gas [m/s] | 301 | 150 | 334 | 130 | 150 |
| Flow rate of chlorine [Nm³/H] | 200 | 800 | 630 | 100 | 400 |
| Flow rate of propylene [Nm³/H] | 920 | 3680 | 2895 | 460 | 1840 |
| Molar ratio [—] | 4.6 | 4.6 | 4.6 | 4.6 | 4.6 |
| Reaction temperature [°C.] | 475 | 475 | 475 | 475 | 475 |
| Selectivity for allyl chloride [mol %] | 91.0 | 91.2 | 91.5 | 90.8 | 89.7 |
| Selectivity for 1,2-dichloropropene [mol %] | 2.6 | 2.6 | 2.6 | 2.6 | 3.2 |
| Selectivity for 1,3-dichloropropene [mol %] | 3.3 | 3.3 | 3.5 | 3.3 | 3.3 |
| Amount of carbon formed (color tone of a concentrated solution) | clear | clear | clear | pale yellow | pale yellow |

| Run No. | Examples | | | | Comparative Examples |
|---|---|---|---|---|---|
| | 6 | 7 | 8 | 9 | 10 (double-tube-type nozzle) |
| L [mm] | 51 | 100 | 96 | 238 | 0 |
| dc [mm] | 3.0 | 5.0 | 10.1 | 2.9 | 35.0 |
| dp [mm] | 5.5 | 7.5 | 22.0 | 6.6 | 65.0 |
| Number of propylene injection openings | 30 | 26 | 12 | 40 | 1 |
| Number of chlorine injection openings | 30 | 26 | 12 | 40 | 1 |
| L/(dp + dc) | 6 | 8 | 3 | 25 | 0 |
| Position of propylene injection openings | outside | outside | outside | outside | outside |
| Position of chlorine injection openings | inside | inside | inside | inside | inside |
| Injecting directions $\theta$ [°] | 10 | 8 | 5 | 5 | 0 |
| Linear velocity of chlorine gas [m/s] | 120 | 90 | 61 | 146 | 100 |
| Linear velocity of propylene gas [m/s] | 250 | 280 | 90 | 199 | 289 |

TABLE 1-continued

| | | | | | |
|---|---|---|---|---|---|
| Flow rate of chlorine [Nm³/H] | 130 | 236 | 300 | 200 | 500 |
| Flow rate of propylene [Nm³/H] | 600 | 1086 | 1380 | 920 | 2300 |
| Molar ratio [—] | 4.6 | 4.6 | 4.6 | 4.6 | 4.6 |
| Reaction temperature [°C.] | 475 | 475 | 475 | 475 | 475 |
| Selectivity for allyl chloride [mol %] | 91.1 | 91.3 | 87.2 | 87.4 | 86.4 |
| Selectivity for 1,2-dichloropropene [mol %] | 2.6 | 2.6 | 3.9 | 4.2 | 5.4 |
| Selectivity for 1,3-dichloropropene [mol %] | 3.4 | 3.2 | 3.5 | 3.2 | 4.2 |
| Amount of carbon formed (color tone of a concentrated solution) | clear | clear | black | black | black |

What we claim is:

1. A process for the production of allyl chloride, which comprises introducing propylene and chlorine into a reactor having at least one propylene-injection opening and at least one chlorine-injection opening, these openings being independent of each other, through the respective injection openings, and reacting them in a vapor phase, wherein propylene and chlorine are introduced into the reactor by injecting them in almost the same direction from the propylene-injection opening and the chlorine-injection opening which is closest to said propylene-injection opening, with a linear velocity in the propylene-injection opening, calculated as a value of at 300° C. and 1 kg/cm².G, of 100 m/sec or higher and a linear velocity of the chlorine-injection opening, calculated as a value of at 100° C. and 1 kg/cm².G, of 70 m/sec or higher, and the propylene-injection opening and the chlorine-injection opening are situated to meet the following expression (1), $$0.5 \leq L/(dp+dc) \leq 20 \quad (1)$$

wherein dp is a diameter of the propylene-injection opening, dc is a diameter of the chlorine-injection opening which is closest to said propylene-injection opening, and L is a distance between centers of these two injection openings.

2. The process of claim 1 wherein dp, dc and L meet the following expression (2).

$$1 \leq L/(dp+dc) \leq 10 \quad (2)$$

3. The process of claim 1 wherein the linear velocities in the injection openings for propylene and chlorine are 130 to 370 m/sec and 80 to 200 m/sec, respectively.

4. The process of claim 1 wherein a line indicating the injecting direction of propylene and a line indicating the injecting direction of chlorine form a flat surface, and an angle formed by these lines is within 30°.

5. The process of claim 1 wherein a nozzle is mounted on the reactor and provided with a plurality of injection openings for propylene and a plurality of injection openings for chlorine.

6. The process of claim 5 wherein the tip of the nozzle is nearly flat, and the plurality of the injection openings for propylene and the plurality of the injection openings for chlorine are arranged in the flat surface.

7. The process of claim 5 wherein the tip of the nozzle is nearly conical, and the plurality of the injection openings for propylene and the plurality of the injection openings for chlorine are arranged in the conical side surface.

8. The process of claim 5 wherein the propylene-injection openings and the chlorine-injection openings are arranged circularly so as to form a concentric circle.

9. The process of claim 5 wherein the number of the propylene-injection openings is the same as the number of the chlorine-injection openings.

* * * * *